United States Patent
Treado et al.

(10) Patent No.: US 11,668,653 B2
(45) Date of Patent: Jun. 6, 2023

(54) RAMAN-BASED IMMUNOASSAY SYSTEMS AND METHODS

(71) Applicant: ChemImage Corporation, Pittsburgh, PA (US)

(72) Inventors: Patrick Treado, Pittsburgh, PA (US); Shona Stewart, Pittsburgh, PA (US); Aaron Smith, Pittsburgh, PA (US); Heather Gomer, Sewickley, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 1338 days.

(21) Appl. No.: 15/776,649

(22) PCT Filed: Nov. 16, 2016

(86) PCT No.: PCT/US2016/062361
§ 371 (c)(1),
(2) Date: May 16, 2018

(87) PCT Pub. No.: WO2017/087574
PCT Pub. Date: May 26, 2017

(65) Prior Publication Data
US 2018/0348136 A1    Dec. 6, 2018

Related U.S. Application Data

(60) Provisional application No. 62/255,804, filed on Nov. 16, 2015.

(51) Int. Cl.
*G01N 21/65*    (2006.01)
*G01J 3/44*    (2006.01)
(Continued)

(52) U.S. Cl.
CPC ............ *G01N 21/65* (2013.01); *G01J 3/0218* (2013.01); *G01J 3/0291* (2013.01); *G01J 3/2823* (2013.01);
(Continued)

(58) Field of Classification Search
CPC .......... G01J 3/44; G01J 3/0218; G01N 21/17; G01N 21/65; G01N 33/574; G01N 33/53
See application file for complete search history.

(56) References Cited

U.S. PATENT DOCUMENTS 7,990,533 B2   8/2011  Maier et al.
8,167,794 B2   5/2012  Matsumoto et al.
(Continued)

FOREIGN PATENT DOCUMENTS

WO    2014007759 A1    1/2014
WO    2014074569 A1    5/2014

OTHER PUBLICATIONS

First Office Action for China Patent Application No. 201680079085.4 issued by the China National Intellectual Property Administration dated Jan. 14, 2020. (with English Translation).
(Continued)

*Primary Examiner* — David P Porta
*Assistant Examiner* — Fani Polyzos Boosalis
(74) *Attorney, Agent, or Firm* — DLA Piper LLP (US)

(57) ABSTRACT

This disclosure is directed to systems and methods for fusing Raman data with biomarker data to identify a disease and/or the progression of the disease. The system disclosed herein may include an illumination source for generating interacted photons from a biological sample and a detector for detecting the interacted photons to generate a Raman data set. A processor is included to fuse the Raman data set with a biomarker data set to identify a disease and/or a disease progression. The instant disclosure further includes a
(Continued)

method comprising illuminating a biological sample to generate interacted photons, and detecting the interacted photons to generate a Raman data set. A biomarker data set is obtained from the biological sample, and the Raman data set is fused with the biomarker data set to generate an index score. The index score correlates with one or more of a disease and a disease progression.

51 Claims, 10 Drawing Sheets

(51) Int. Cl.
    *G01N 21/17*     (2006.01)
    *G01J 3/02*     (2006.01)
    *G01J 3/28*     (2006.01)
    *G16H 50/20*     (2018.01)
    *G01N 33/53*     (2006.01)

(52) U.S. Cl.
    CPC ............... *G01J 3/44* (2013.01); *G01N 21/17* (2013.01); *G01N 33/53* (2013.01); *G16H 50/20* (2018.01); *G01N 2201/0833* (2013.01); *G01N 2800/50* (2013.01); *G01N 2800/52* (2013.01); *G01N 2800/56* (2013.01); *G01N 2800/60* (2013.01)

(56) References Cited

U.S. PATENT DOCUMENTS

| | | |
|---|---|---|
| 2007/0086003 A1 | 4/2007 | Maier et al. |
| 2007/0206185 A1 | 9/2007 | Tuschel et al. |
| 2008/0032420 A1 | 2/2008 | Lambert et al. |
| 2012/0083678 A1 | 4/2012 | Drauch et al. |
| 2013/0003044 A1 | 1/2013 | Maier et al. |
| 2013/0176568 A1 | 7/2013 | Priore et al. |
| 2015/0153341 A1 | 6/2015 | Lee et al. |
| 2015/0294076 A1 | 10/2015 | Treado et al. |
| 2016/0213252 A1 | 7/2016 | Hillman et al. |
| 2018/0348136 A1* | 12/2018 | Treado .................. G01J 3/2823 |

OTHER PUBLICATIONS

Chen, "Inspection Technology of Animal-Derived Food," China Agricultural University Press, Feb. 28, 2014.
International Search Report and Written Opinion of the ISR for PCT/US2016/062361 dated Jan. 30, 2017.
Wang et al., Three-Dimensional Imaging of Ureter With Endoscopic Optical Coherence Tomography, Urology (May 2011), 77(5):1254-1258.
Bar-Or et al., "Raman spectral signatures of human liver perfusates correlate with oxidation reduction potential," Molecular Medicine Reports, Mar. 1, 2009, pp. 175-180.
Extended European Search Report for EP Application No. 16867078.4 dated May 13, 2019.

* cited by examiner

RAMAN-BASED IMMUNOASSAY SYSTEMS AND METHODS

CROSS-REFERENCE TO RELATED APPLICATIONS

This application is a U.S. national stage filing under 35 U.S.C. § 371 of International Application No. PCT/US2016/062361 entitled "Raman-Based Immunoassay Systems and Methods," and filed on Nov. 16, 2016, which claims benefit of and priority under 35 U.S.C. § 119(e) to U.S. Provisional Application No. 62/255,804 entitled "Raman Based Assays," filed Nov. 16, 2015. The contents of each of these applications are incorporated herein by reference in their entireties.

BACKGROUND

Cancer is significant, not only in terms of mortality and morbidity, but also in terms of the cost of treating advanced cancers and reduced productivity and quality of life of advanced cancer patients. Despite the common conception of cancers as incurable diseases, many cancers can be alleviated, slowed, or even cured if timely medical intervention is administered.

Cancers arise by a variety of mechanisms, not all of which are understood. Cancers, called tumors when they arise in the form of a solid mass, characteristically exhibit decontrolled cell growth and/or proliferation. Cancer cells often exhibit other characteristic differences relative to the cell type from which they arise, including altered expression of cell surface, secreted, nuclear, and/or cytoplasmic proteins, altered antigenicity, altered lipid envelope (i.e., cell membrane) composition, altered nucleic acid production, altered morphology, and other differences. Typically, cancers are diagnosed either by observing tumor formation or by observing one or more of these characteristic differences. Because cancers arise from cells of normal tissues, cancer cells may initially closely resemble the cells of the original normal tissue, often making detection of cancer cells difficult until the cancer has progressed to a stage at which the differences between cancer cells and the corresponding original normal cells are more pronounced. Certain types of cancer can advance to a relatively difficult-to-treat stage before they are easily detectable.

Early definitive detection and classification of cancer is often crucial to successful treatment. Included in the diagnosis of many cancers is a determination of the type and grade of the cancer and the stage of its progression. This information can inform treatment selection, allowing use of milder treatments (i.e., having fewer undesirable side effects) for relatively early-stage, non- or slowly-spreading cancers, and more aggressive treatment (i.e., having more undesirable side effects and/or a lower therapeutic index) of cancers that pose a greater risk to the patient's health.

When cancer is suspected, a physician will often have the tumor or a section of abnormal tissue removed or biopsied and sent for histopathological analyses. Typically, the time taken to prepare the specimen is on the order of one day or more. Communication of results from the pathologist to the physician and to the patient can further slow the diagnosis of the cancer, and the onset of any indicated treatment. Patient anxiety can soar during the period between sample collection and diagnosis.

Advancements in immunoassay development have led to identification of a large number of biomarkers for disease states. While some biomarkers have limited useful clinical significance, there are examples where a single biomarker is sufficient to diagnose a specific disease state, such as HIV-1. Specific biomarkers include carcinoembryonic antigen (CEA) and prostate specific antigen (PSA). Unfortunately, many complex diseases require multiple biomarkers to produce useful clinical information, and recent studies have indicated that analysis of a single biomarker may be inadequate in the detection and progression of a disease.

Colorectal cancer (CRC) is a slow-developing disease that often begins as a benign abnormal growth on the lining of the colon or rectum. Untreated growths can lead to malignancy and the release of abnormal biomarkers into the blood. These biomarkers may be detectable in the blood, and may be useful as a liquid biopsy tool to screen and diagnose patients non-invasively. CRC is the third most common cancer in the developed world, with over 134,000 new cases and 49,000 deaths predicted annually in the US alone. The disease affects both men and women and is the third leading cause of cancer mortality. CRC survival rates are directly related to progression stage at detection. When detected early, the five-year survival rate is greater than 95%, but the survival rate for late stage discovery is around 5%. The National Cancer Institute estimates that 5% of Americans will be diagnosed with CRC during their lifetime. While colonoscopy remains the recommended screening procedure, there is a risk of complications, including bowel tearing and bleeding, which are heightened during polyp removal.

The cost of CRC care in the United States is dependent on the stage at which CRC is detected, with early stage treatment being the most cost-effective. However, the cost, risk, and discomfort associated with an invasive colonoscopy and stool collection contribute to low participation in CRC screening. CRC management is a global issue, and a reliable and non-invasive detector of disease and its progression would be an asset to the medical community.

Another important area for non-invasive early detection relates to prostate cancer. Currently, a man dies from prostate cancer every 19 minutes. Adenocarcinoma of the prostate is the most common non-skin cancer in men, and the second leading cause of death from cancer in males. Although prostate cancer is a leading cause of cancer death in males, the high prevalence of the disease indicates that most men with prostate cancer do not die from the disease. The clinical challenge is differentiating those patients with aggressive disease from those with a more indolent variety, i.e., accurately characterizing the risk the cancer poses. The current inability to characterize the disease has led to unnecessarily aggressive treatment in some cases. Thus, there is an intense need to improve the prediction of the presence and progression of the disease to enhance treatment decision making. PSA is a sensitive serum marker for prostate cancer. However, PSA has been shown to have poor specificity, leading to over-diagnosis of prostate cancer.

Thus, a recognized need exists to shorten the time required to analyze biological samples in order to identify cancer and its progression with a high specificity. Furthermore, it would be beneficial to use body fluids instead of traditional tissue/cellular samples, in order to minimize invasive surgery and unnecessary medical treatment.

SUMMARY

The instant disclosure relates to systems and methods for combining Raman data and biomarker data from a biological sample to identify a disorder or disease and/or a progression of the disorder or disease. In one embodiment, a system may include an illumination source configured to illuminate a biological sample and generate a plurality of interacted photons. A detector is configured to detect the plurality of interacted photons and generate at least one Raman data set. A processor may be configured to fuse the at least one Raman data set with at least one biomarker data set to identify one or more of a disorder, disease and a progression of the disease and/or disorder. In another embodiment, the plurality of interacted photons may be passed through a fiber array spectral translator device configured to receive the plurality of the interacted photons and generate an optical output. The fiber array spectral translator may include a first end comprising a two-dimensional plurality of optical fibers and a second end having a one-dimensional stack of the plurality of optical fibers. In one embodiment, a spectrometer is optically coupled to the one-dimensional stack of the fiber array spectral translator and is configured to filter the optical output into a plurality of wavelengths.

In one embodiment, a method may include illuminating a biological sample to generate a plurality of interacted photons. The plurality of interacted photons may be detected to generate at least one Raman data set. The method further includes obtaining at least one biomarker data set from the biological sample, and fusing the at least one Raman data set with the at least one biomarker data set to generate an index score. The index score may include an indication of the presence of a disease and a progression of the disease. In another embodiment, the method may include passing a plurality of interacted photons through a fiber array spectral translator.

DETAILED DESCRIPTION

Figure 1:
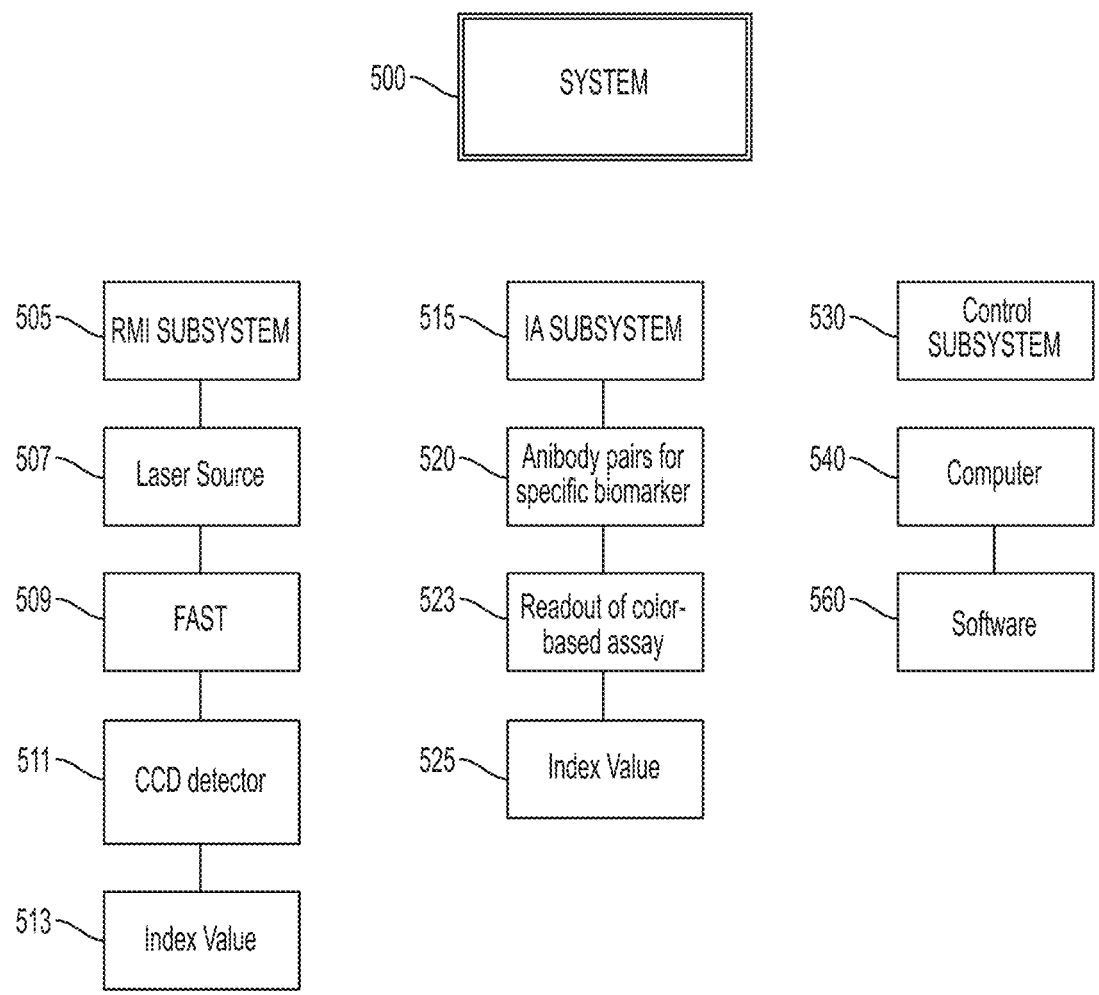
FIG. 1 illustrates a system in accordance with the instant disclosure.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "sample" is a reference to one or more samples and equivalents thereof known to those skilled in the art, and so forth.

As used herein, the term "about" means plus or minus 10% of the numerical value of the number with which it is being used. Therefore, about 50% means in the range of 40% to 60%.

The instant disclosure relates to systems and methods for analyzing a biological sample or components thereof by fusing one or more Raman spectral data sets with one or more biomarker data sets to generate an index score. In one embodiment, the index score comprises a Raman immunoassay index score. The Raman immunoassay index score may comprise a score indicative of one or more of a disease, a disorder, a disease state, and a disorder state. The state of a disease or disorder may be referred to as a progression. The progression of a disease may include the extent to which a disease has developed, for example, a disease stage. In one embodiment, the disease stage may include a cancer stage. The Raman immunoassay index score may be a scalable metric where a higher index score correlates to a more persistent and developed disease.

In one embodiment, a biological sample may be analyzed to determine one or more of a disease, a disorder, a disease state and a disorder state. Examples of biological samples suitable for analysis herein include, without limitation, a bodily fluid such as urine, saliva, sputum, feces, blood, serum, plasma, sweat, mucus, pus, semen, fluid expressed from a wound, lavage, cerebrospinal fluid, vaginal fluid, and combinations thereof. Although this disclosure focuses on determining a disease state, i.e., presence of the disease and/or a progression stage of the disease, of a biological sample, the present disclosure also contemplates that the systems and methods disclosed herein may be used to determine other characteristics of a sample (e.g. a metabolic state, a hydration state, an inflammatory state, and combinations thereof) and/or precursor conditions within the definition of disease state. Additionally, while the examples provided herein relate to the detection of colorectal cancer and prostate cancer, the present disclosure is not limited to these cancers. The systems and methods described herein may be used to analyze a wide variety of cancers and other diseases, including autoimmune disorders and neurodegenerative disorders, as would be apparent to one of skill in the art in view of this disclosure. In addition to detecting the presence of cancer in a biological sample, the systems and methods described herein may also be applied to determine a cancer grade and/or stage.

The term "biomarker" as used herein refers to a measurable substance in a biological sample for which its presence is indicative of some phenomenon, such as, without limitation, disease, infection, inflammation, immune response and/or environmental exposure. In one embodiment, the biomarker includes a cancer biomarker. In another embodiment, the biomarker includes a DNA sequence and a protein.

In one embodiment, the biomarker includes CEA. In another embodiment, the biomarker includes PSA. Other biomarkers may be suitable for use in embodiments of the instant disclosure, and such biomarkers would be apparent to one of skill in the art in view of this disclosure. In one embodiment, a blood or serum sample may be analyzed for either CEA or PSA, and the analysis may result in a biomarker index score. A biomarker index score may include a measurement of the amount of the biomarker per milliliter of blood. For instance, PSA is expressed in nanograms per milliliter of blood (ng/ml), and CEA is expressed in micrograms per liter of blood (μg/L). A biomarker index score of less than about 4.0 ng/ml of PSA is considered normal. Above such a value, a prostate biopsy may be recommended. In the case of CEA, a biomarker index score of above about 2.5 μg/L may be indicative of colorectal cancer. However, biomarker index scores alone have been shown to be inadequate in positively diagnosing a disease. A false positive may result in a patient having to undergo an invasive biopsy in order to have a complete diagnosis.

In one embodiment, a biomarker index score (optionally referred to herein as a biomarker data set) may be fused with a Raman data set for generating a Raman immunoassay index score. In one embodiment, the biomarker data set includes a biomarker index. The Raman immunoassay index score disclosed herein provides information with a greater specificity and a greater sensitivity then either a biomarker data set or Raman data set alone.

Raman molecular imaging (RMI) involves collection of multiple spatially resolved Raman spectra combined with digital imaging. RMI allows for collection of quantitative information that can be used for objective analysis rather than the subjective analysis common to clinical microscopy techniques, such as histopathology. Instruments for performing RMI typically comprise a laser source, an image gathering optic and an imaging detector. Importantly, RMI is a reagentless tool which reduces the cost per assay compared to other methodologies. An automated algorithm preprocesses the spectra using routines that may include, for example, baseline correcting, vector normalizing, filtering out cosmic events, and classifying highly fluorescent or abnormal spectra as outliers.

In one embodiment, a Raman data set and the biomarker data set may be obtained separately and fused to generate a Raman immunoassay index score. In another embodiment, the Raman data set and biomarker data set may be obtained substantially simultaneously. In one embodiment, the Raman data may be obtained by a commercially available Raman spectroscopy microscope, as is known to those of skill in the art. Known Raman devices, although suitable for use in embodiments descried herein, require lengthy times to acquire replicate Raman spectra on the order of about 90 seconds per spectra. Typically, up to 15 replicate Raman spectra are obtained per Raman data set. Thus, conventional systems may have acquisition times for a Raman data set of up to or exceeding 30 minutes. In another embodiment, the Raman data set may be obtained using a Raman device configured to capture a Raman data set in less than about 10 minutes. In another embodiment, the Raman data set is acquired in less than about 7 minutes. In another embodiment, the Raman data set is acquired in less than about 5 minutes. In another embodiment, the Raman data set is acquired in less than about 3 minutes.

FIG. 1 illustrates a system 500 according to an embodiment. The system 500 may include a Raman imaging subsystem 505, an immunoassay subsystem 515 and a control subsystem 530. The Raman imaging subsystem 505 may include a laser illumination source 507 for illuminating a biological sample (not shown), and FAST fiber bundle 509. In some embodiments, the Raman imaging subsystem may exclude a FAST fiber bundle. The Raman imaging subsystem 505 may further include a CCD detector 511 for detecting photons which have interacted with the biological sample. Raman molecular image data may be collected from the Raman imaging subsystem 505. In one embodiment, Raman molecular image data can be collected using dried samples on a background such as aluminum coated slides (not shown). In one embodiment, multiple samples may be presented on a slide, and regions of interest may be identified.

The system 500 may further include a control subsystem 530. The control subsystem 530 may include a computer processor 540 and machine readable code or software 560 in communication with the computer processor 540. In one embodiment, the control subsystem 560 may control the collection of data from the Raman imaging (RMI) subsystem 505 and the immunoassay subsystem 515. In another embodiment, the control system 530 may control the RMI subsystem 505 and the immunoassay subsystem 515 to capture a Raman molecular image and immunoassay data at about the same time. By collecting the RMI data and immunoassay data at about the same time, effects related to sample storage and sample quality may be negated. In one embodiment, the control subsystem 560 controls one or more of the collection of data from identified regions of interest, processes spectra, applies algorithms to reject fluorescence and other unsuitable spectral data, and applies one or more algorithms to calculate a Raman index value 513 and an immunoassay index value 525.

The system 500 may further include an immunoassay subsystem 515. The immunoassay subsystem 515 may include antibody pairs for a specific biomarker 520. An immunoassay test result may include color readout of a color-based assay 523, and an index value 525 may be generated. In one embodiment, the immunoassay subsystem 515 may operate using liquid samples in a multi-well plate (not shown) configured to capture immunoassay data in a "sandwich" format or a multi-well stack. In one embodiment, the multi-well plate is coated with a capture antibody, and the biological sample is incubated in the wells of the multi-well plate. Portions of the biological sample that are unbound with the antibodies may be removed through washing. One or more detection antibodies specific to the tested biomarker may be added. Further, an enzyme-like secondary antibody that contains a color-based reporter component may be added to report a color value for the immunoassay index value 525. In one embodiment, the control subsystem 530 may be configured to convert the color intensity of the color-based reporter to the index value 525.

Figure 2:
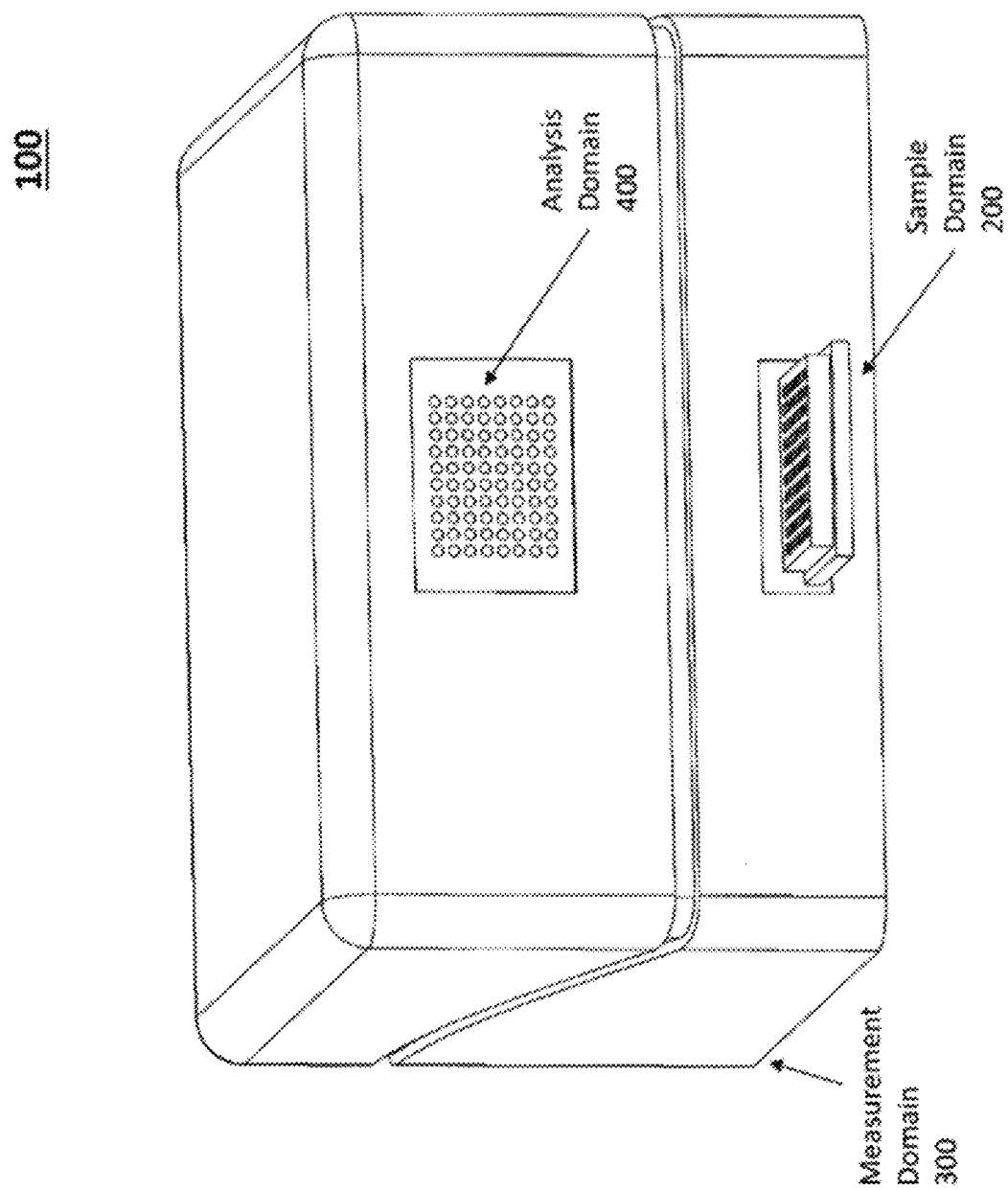
FIG. 2 illustrates a housing configuration of a Raman-based system in accordance with the instant disclosure.
Figure 3A:
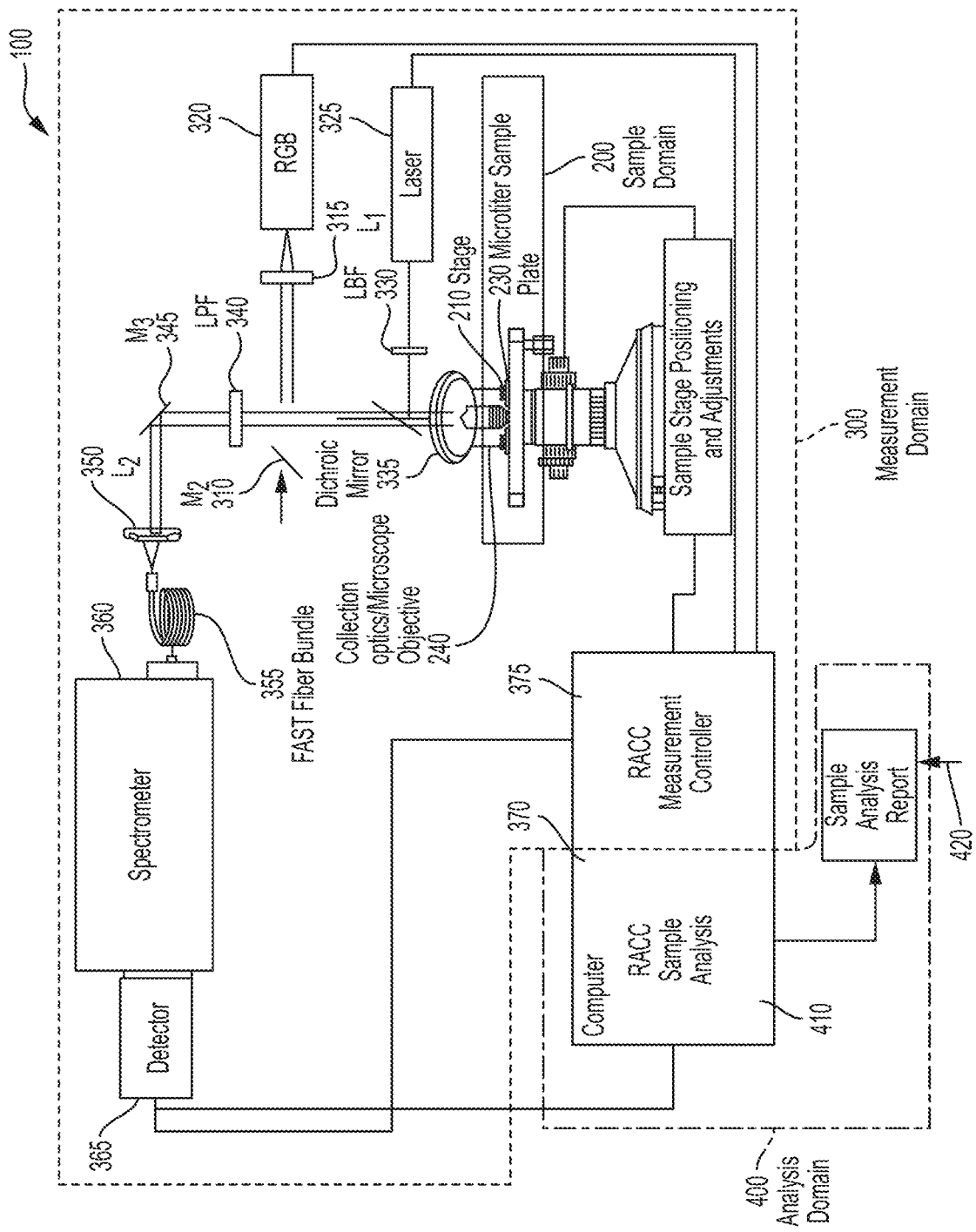
FIG. 3A illustrates a Raman-based system in accordance with the instant disclosure.
Figure 3B:
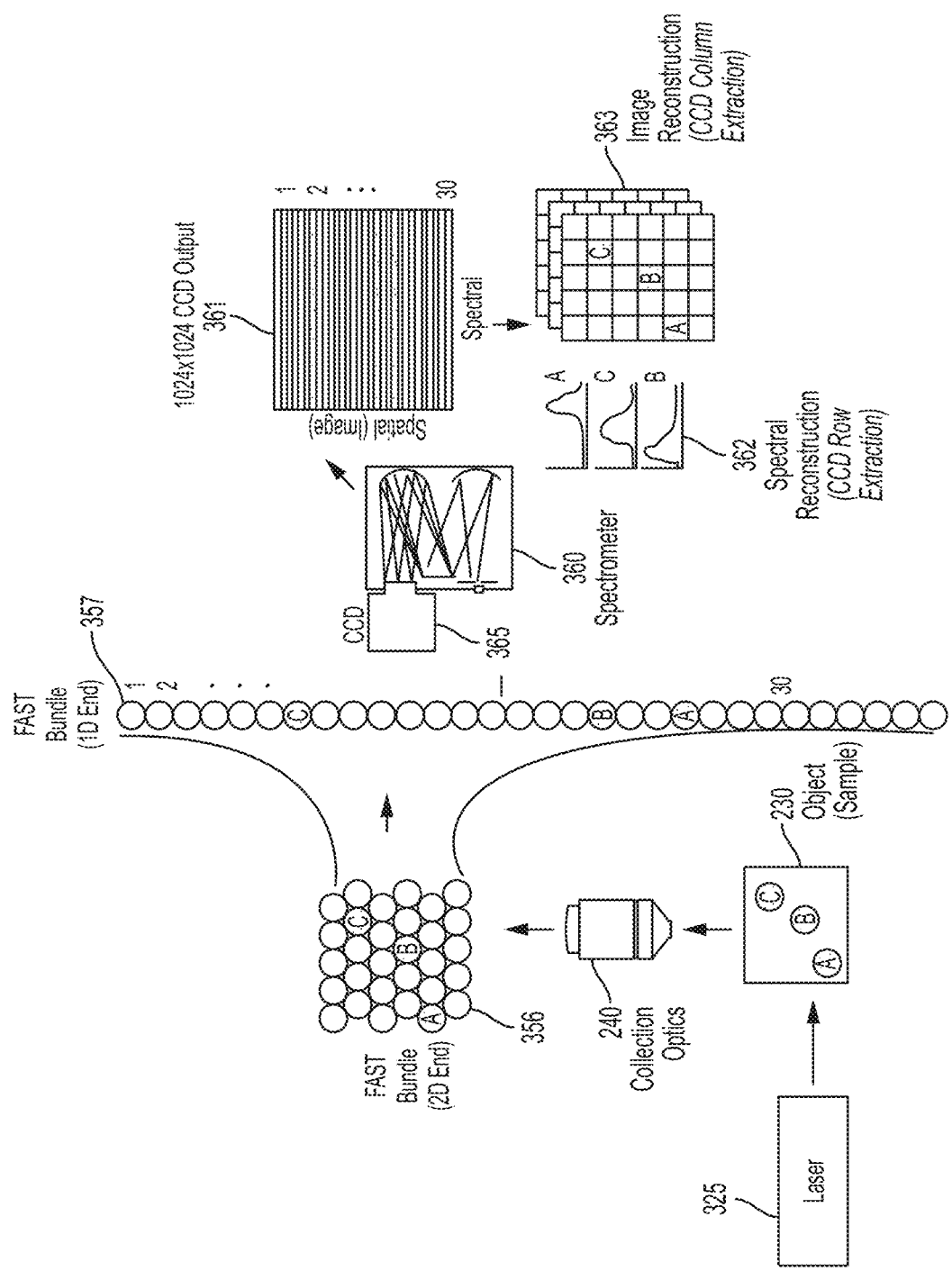
FIG. 3B illustrates a fiber array spectral translator (FAST) device in accordance with the instant disclosure.

FIGS. 2, 3A and 3B provide an illustrative device having a Raman subsystem for use in obtaining a Raman data set according to an embodiment. This device is further detailed in U.S. Patent Application Publication Number 2015/0294076 entitled SYSTEM AND METHOD FOR SERUM BASED CANCER DETECTION, and assigned to Chemimage Corporation. This application is incorporated herein in its entirety.

The device of FIGS. 2, 3A and 3B includes an exemplary housing of a system 100 as illustrated in FIG. 2. The system 100 may comprise a sample domain 200 for placing a sample under analysis, a measurement domain 300, for generating at least one Raman data set of the sample placed in the sample domain 200, and an analysis domain 400 for analyzing the data generated by the measurement domain 300.

FIG. 3A is a more detailed representation of a system 100 according to an embodiment. As illustrated in FIG. 3A, the sample domain 200 may further comprise a stage 210 for placing a sample. This stage 210 may be moved to analyze the various samples under analysis. In one embodiment, the sample may be affixed to a slide or placed in a well plate, such as a microtiter sample plate 230. The sample may be placed under collection optics such as a microscope objective 240 for analysis.

The measurement domain 300 may comprise an RGB camera 320 configured to generate an RGB image representative of the sample. At least one mirror 310 may be configured to direct photons from the sample through at least one lens 315 to the RGB camera 320. The RGB image generated may be used to help align the sample for analysis and/or to find morphological features or areas of interest in the sample. The RGB image may also be correlated with a Raman data set generated by the measurement domain 300.

Still referring to FIG. 3A, the measurement domain 300 may further comprise at least one laser illumination source 325 configured to emit illuminating photons that may be passed through a laser bandpass filter (LBF) 330 to filter out wavelengths of light that are not of interest and allow one or more wavelengths of light of interest to pass through. These filtered illuminating photons may be directed to the sample by at least one mechanism 335 such as a dichroic mirror or a dichroic beamsplitter.

The illuminating photons may illuminate the sample and generate at least one plurality of interacted photons. As used herein "interacted photons" may comprise photons scattered by the sample, photons absorbed by the sample, photons reflected by the sample, photons emitted by the sample, and combinations thereof.

A plurality of interacted photons may be passed through a long pass filter (LPF) 340 to filter out photons having short wavelengths and directed by at least one mirror 345 through a lens 350 to a two-dimensional end of a fiber array spectral translator (FAST) device 355. A FAST device 355 is illustrated in more detail in FIG. 3B.

In FIG. 3B, the FAST device 355 comprises a two-dimensional end 356 and a one-dimensional end 357. In one embodiment, the two-dimensional end 356 may have an ordering, such as serpentine ordering. The two-dimensional end 356 of the FAST device 355 may comprise a two-dimensional array of optical fibers drawn into a one-dimensional fiber stack 357. In one embodiment, the two-dimensional end 365 may be non-linear (which can be in any non-linear configuration, e.g., circular, square, rectangular, etc.) and the one-dimensional linear end 357 may be linear.

At least a portion of the interacted photons may be focused onto the input (two-dimensional end 365) of a FAST device, which may include of up to thousands of individual fibers, each fiber collecting the light scattered (or absorbed, reflected, and/or emitted) by a specific corresponding location in the excited area of a biological sample. In another embodiment, the FAST device may include less than about 100 fibers. In another embodiment, the FAST device may have about 96 fibers.

The one-dimensional fiber stack 357 (output end) may be orientated at the entrance slit of a spectrometer 360, illustrated in FIG. 3B. The spectrometer 360 can function to separate the plurality of photons into a plurality of wavelengths and provide a separate dispersive spectrum from each fiber. Multiple Raman spectra and, therefore, multiple interrogations of the sample area can be obtained in a single measurement cycle. Inclusion of the FAST device permits the system 100 to capture multiple Raman spectra in about the same amount of time that it takes for a conventional Raman sensor to collect one spectrum. Thus, the FAST device permits a considerable reduction in acquisition time.

Referring again to FIG. 3B, photons may be detected at a detector 365 to generate a Raman data set. In one embodiment, a processor (and/or software) 370 may be used to extract spectral/spatial information that is embedded in a single frame generated by a detector 365.

Referring to FIG. 3B, 361 is representative of an exemplary detector 365 output, 362 is representative of an exemplary spectral reconstruction, and 363 is representative of an exemplary image reconstruction.

In one embodiment, an area of interest can be optically matched by the FAST device to an area of a laser spot to maximize the collection Raman efficiency. In one embodiment, the present disclosure contemplates a configuration in which only the laser beam is moved for scanning within a field of view (FOV). The present disclosure also contemplates an embodiment in which the sample is moved and the laser beam is stationary.

It is possible to optically match the "scanning" FOV with the Raman collection FOV. The FOV is imaged onto a rectangular FAST device so that each FAST fiber is collecting light from one region of the FOV. The area per fiber which yields the maximum spatial resolution is easily calculated by dividing the area of the entire FOV by the number of fibers. Raman scattering is only generated when the laser excites a sample, so Raman spectra will only be obtained at those fibers whose collection area is being scanned by the laser beam. Scanning only the laser beam is a rapid process that may utilize off-the-shelf galvanometer-driven mirror systems.

The construction of the FAST device 355 requires knowledge of the position of each fiber at both the two-dimensional end 356 and the distal end, one-dimensional end 357 of the array. Each fiber collects light from a fixed position in the two-dimensional array (imaging end) and transmits this light onto a fixed position on the detector 365 (through that fiber's distal end 357).

Each fiber may span more than one detector row, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

One of the fundamental advantages of using a FAST device, over other spectroscopic methods, is speed of analysis. FAST technology can acquire a few to thousands of full-spectral-range, spatially resolved spectra simultaneously. A complete spectroscopic imaging data set can be acquired in the amount of time it takes to generate a single spectrum from a given material using conventional means, especially for samples that are susceptible to laser-induced photodamage. FAST devices can also be implemented with multiple detectors, and color-coded FAST spectroscopic images can be superimposed on other high-spatial resolution gray-scale images to provide significant insight into the morphology and chemistry of the sample.

Utilizing a FAST device is one way of configuring a system 100 for what may be referred to as "multipoint"

analysis. To perform multipoint analysis, the biological sample and field to be evaluated is illuminated in whole or in part, depending on the nature of the biological sample and the type of multipoint sampling desired. A field of illumination can be divided into multiple adjacent, non-adjacent, or overlapping points, and spectra can be generated at each of the points. In one embodiment, these spectra may be averaged. In another embodiment, an illumination spot size can be increased sufficiently to spatially sample/average over a large area of the sample. This may also include transect sampling.

By way of example, the entire sample can be illuminated and multipoint analysis performed by assessing interacted photons at selected points. Alternatively, multiple points of the sample can be illuminated, and interacted photons emanating from those points can be assessed. The points can be assessed serially (i.e., sequentially). To implement this strategy, there is an inherent trade-off between acquisition time and the spatial resolution of the spectroscopic map. Each full spectrum takes a certain time to collect. As more spectra are collected per unit area of a sample, both the apparent resolution of the spectroscopic map, the data acquisition time increases. In another embodiment, interacted photons can be assessed in parallel (i.e., simultaneously) for all selected points in an image field. This parallel processing of all points is designated chemical imaging, and can require significant data acquisition time, computing time and capacity when very large numbers of spatial points and spectral channels are selected. However, if may require less data acquisition time, computing time and capacity when a relatively small number of spectral channels are assessed.

In one embodiment, interacted photons may be assessed at multiple points in a FOV (e.g., the field of magnification for a microscope) that together represent only a portion of the area of the FOV (multipoint). It has been discovered that sampling the FOV at points representing a minority of the total area of the field (e.g., at two, three, four, six, ten, fifty, one hundred, or more and/or points representing, in sum, 25%, 5%, 1%, or less of the field) may provide a valuable representation of the FOV. The points can be single pixels of an image of the FOV or areas of the field represented in an image by multiple adjacent or grouped pixels. The shape of areas or pixels assessed as individual points is not critical. For example, circular, annular, square, or rectangular areas or pixels can be assessed as individual points. Lines of pixels may also be assessed in a line scanning configuration.

The area corresponding to each point of a multipoint analysis can be selected or generated in a variety of known ways. In one embodiment, structured illumination may be used. By way of example, a confocal mask or diffracting optical element placed in the illumination or collection optical path can limit illumination or collection to certain portions of the sample having a defined geometric relationship.

Spectroscopic analysis of multiple points in a FOV (multipoint analysis) allows high quality spectral sensing and analysis without the need to perform spectral imaging at every picture element (pixel) of an image. Optical imaging (e.g. RGB imaging) can be performed on the sample (e.g., simultaneously or separately), and the optical image can be combined with selected spectral information to define and locate regions of interest. Rapidly obtaining spectra from sufficiently different locations of this region of interest at one time allows highly efficient and accurate spectral analysis and the identification of components in samples. Furthermore, identification of a region of interest in a sample or in a FOV can be used as a signal that more detailed Raman scattering (or other) analysis of that portion of the sample or FOV should be performed.

The high numbers of optical fibers required for FAST spectroscopic and/or imaging applications place extraordinary demands on the imaging spectrograph, which the multipoint method addresses. Instead of having millions of pixels, multipoint analysis can utilize larger diameter fibers in bundles containing two to thousands of fibers. In the multipoint method of spectral sensing and analysis, complete spectral imaging (which would require at least thousands of adjacent pixels to create a physical image) is not required. Instead, spectral sensing performed at two to thousands of points simultaneously can rapidly (on the order of seconds) provide high quality spatially resolved spectra from a wide variety of points on the sample needed for analysis and identification. Thus, even if the precise geometric arrangement of the points analyzed in the FOV is not known, the points nonetheless have a defined geometrical arrangement which can span a sample or a FOV. The analyzed points may be informative regarding the disease state of a biological sample.

Referring again to FIG. 3A, photons may be delivered to a spectrometer 360 wherein the spectrometer is configured to filter the interacted photons into a plurality of wavelengths. A detector 365 may be configured to generate at least one Raman data set. In one embodiment, the Raman data set may comprise at least one of: at least one Raman spectrum and at least one Raman chemical image. In one embodiment, the detector 365 may further comprise at least one of: a CCD detector, an ICCD detector, a CMOS detector, a PMT, a Si-avalanche photodiode, an InGaAs detector, an InSb detector, and an MCT detector.

The system 100 may further comprise at least one processor 370. The processor 370 may function to carry out various functions in both the measurement domain 300 and the analysis domain 400. In the measurement domain 300, the processor 370 may comprise a measurement controller 375 that may comprise software to control various features of the system 100 such as data acquisition and calibration of the system.

The system 100 may also comprise an analysis domain 400, configured to analyze the data generated by the measurement domain 300. The processor 370 may function in the analysis domain 400 to analyze the Raman data set. An analysis report 420 may be generated based on this analysis. This analysis report 420 may comprise a determination of a disease state of a biological sample under analysis.

In one embodiment, the system 100 may further comprise at least one reference database comprising at least one reference data set, wherein each reference data set is associated with a known disease state. This reference data may be stored in the processor 370 and accessed to analyze the Raman data set generated from the biological sample. The device illustrated in FIGS. 2-3B and other embodiments thereof are further detailed in U.S. Patent Application Publication Number 2015/0294076, and such embodiments may be suitable for use in an embodiment of the instant disclosure.

In one embodiment, at least one Raman data set collected from a biological sample is fused with at least one biomarker data set to form a Raman immunoassay index score. In another embodiment, the at least one biomarker data set includes 1, 2, 3, or 4 biomarkers. In another embodiment, the at least one biomarker data set includes more than 4 biomarkers. In one embodiment, the at least one Raman data set includes a plurality of Raman spectra. In one embodiment, the Raman data set includes a Raman image. In another embodiment, the Raman data set includes at least one Raman spectrum and at least one Raman image. In one embodiment, the Raman data set may include a hyperspectral Raman image.

In one embodiment, the at least one Raman data set is fused with the at least one biomarker data set using an image weighted Bayesian fusion (IWBF) methodology. In one embodiment, Monte Carlo may be used in a training step to find the optimized weights that produce a fused result with detection performance no worse than the detection performance of the best individual test, and with better overall detection performance than any of the individual sensing strategies operating alone.

The Raman immunoassay index score may be used to identify a disease and a disease state having a higher level of performance (sensitivity and specificity) over biomarker test and Raman data alone. Performance can be measured by using a receiver operating characteristic (ROC) curve which can reveal the sensitivity and specificity of the test and the area under the ROC curve (AUC). In one embodiment, the Raman immunoassay includes an AUC of greater than about 5% higher than that of either a Raman data set or a biomarker data set alone. In another embodiment, the Raman immunoassay includes an AUC of greater than about 8%. In another embodiment, the Raman immunoassay includes an AUC of greater than about 10%. The increased performance of the system and methods disclosed herein may be accomplished by fusing at least one Raman data set with one biomarker; however, the performance may be enhanced by combining the Raman data set with more than one biomarker.

Figure 4:
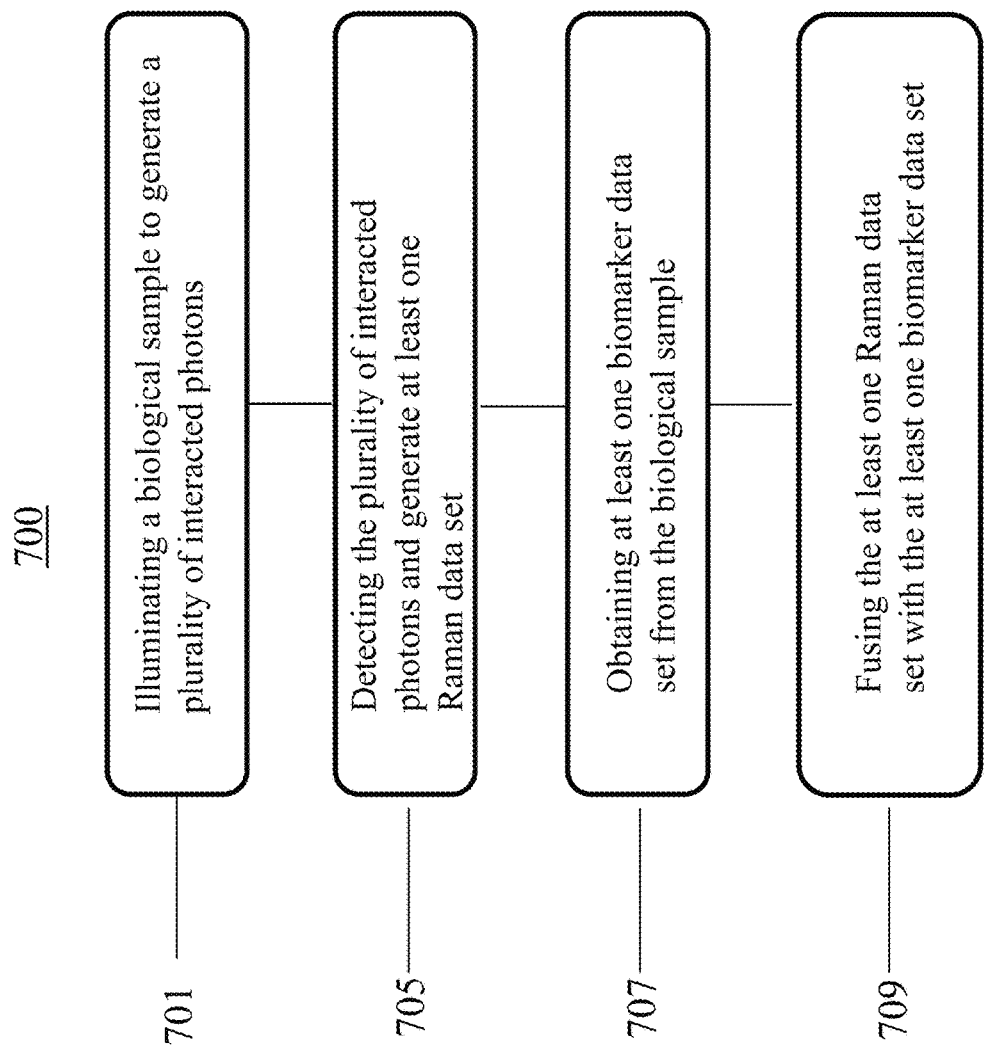
FIG. 4 illustrates a flowchart for a method in accordance with the instant disclosure.

The instant disclosure is further directed to methods for generating a Raman immunoassay. Turning to FIG. 4, in one embodiment, a method 700 includes illuminating 701 a biological sample to generate a plurality of interacted photons. Illuminating may include, illuminating with a laser. In one embodiment, the laser includes a wavelength of about 785 nm. The interacted photons may be detected 705 by a detector to generate at least one Raman data set. In another embodiment, the method may include passing the plurality of interacted photons through a fiber array spectral translator to generate a first optical output, where the first optical output is detected by the detector. The method further includes obtaining 707 at least one biomarker data set from the biological sample, and fusing 709 the at least one Raman data set with the at least one biomarker data set to generate an index score. In one embodiment, the index score is indicative of the presence and/or stage (progression) of a disease or disorder. In another embodiment, the disease is cancer. In another embodiment, the disease may include one or more of prostate or colorectal cancer.

The instant disclosure is further directed to a non-transitory processor readable storage medium containing machine readable program code, which when executed by a processor causes the processor to cause an illumination source to illuminate a biological sample to produce a plurality of interacted photons. In one embodiment, the processor may cause a fiber array spectral translator to collect the plurality of interacted photons and generate an optical output. In another embodiment, the processor may cause a detector to detect one or more of the optical output from the fiber array spectral translator and the plurality of interacted photons and generate at least one Raman data set. In another embodiment, the processor may fuse the at least one Raman data set with at least one biomarker data set and generate an index score. The index score may indicate one or more of the presence of a disease and/or disorder and/or the progression thereof.

In some embodiments, the system may include at least one reference database comprising at least one reference data set. The reference data set may include one or more known data sets associated with known Raman spectroscopy and imaging data, known biomarker immunoassay data and known fused data sets comprising known fused data from at least one Raman data set and at least one biomarker data set. In one embodiment, the system may access the known reference database to identify a disease and/or disorder, including a state or progression of the disease and/or disorder. Further, the system may access a known reference database to identify a Raman immunoassay index score based on a fused data set of at least one Raman data set and at least one biomarker data set.

EXAMPLES

Example 1

Figure 5:
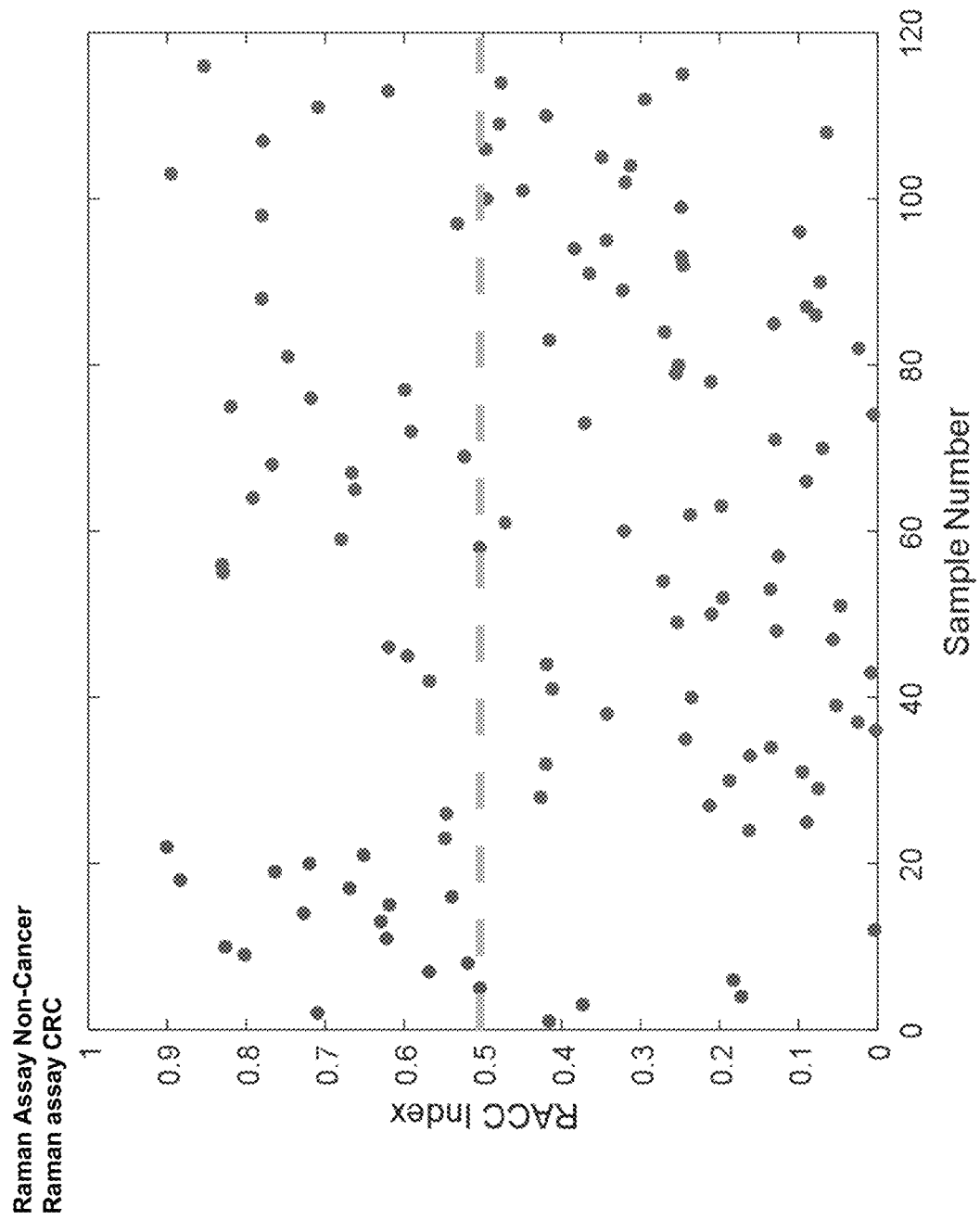
FIG. 5 illustrates a discrimination plot representing Raman as a standalone methodology including Raman indices for colorectal cancer (CRC) and non-cancer blood samples in accordance with the instant disclosure.
Figure 6:
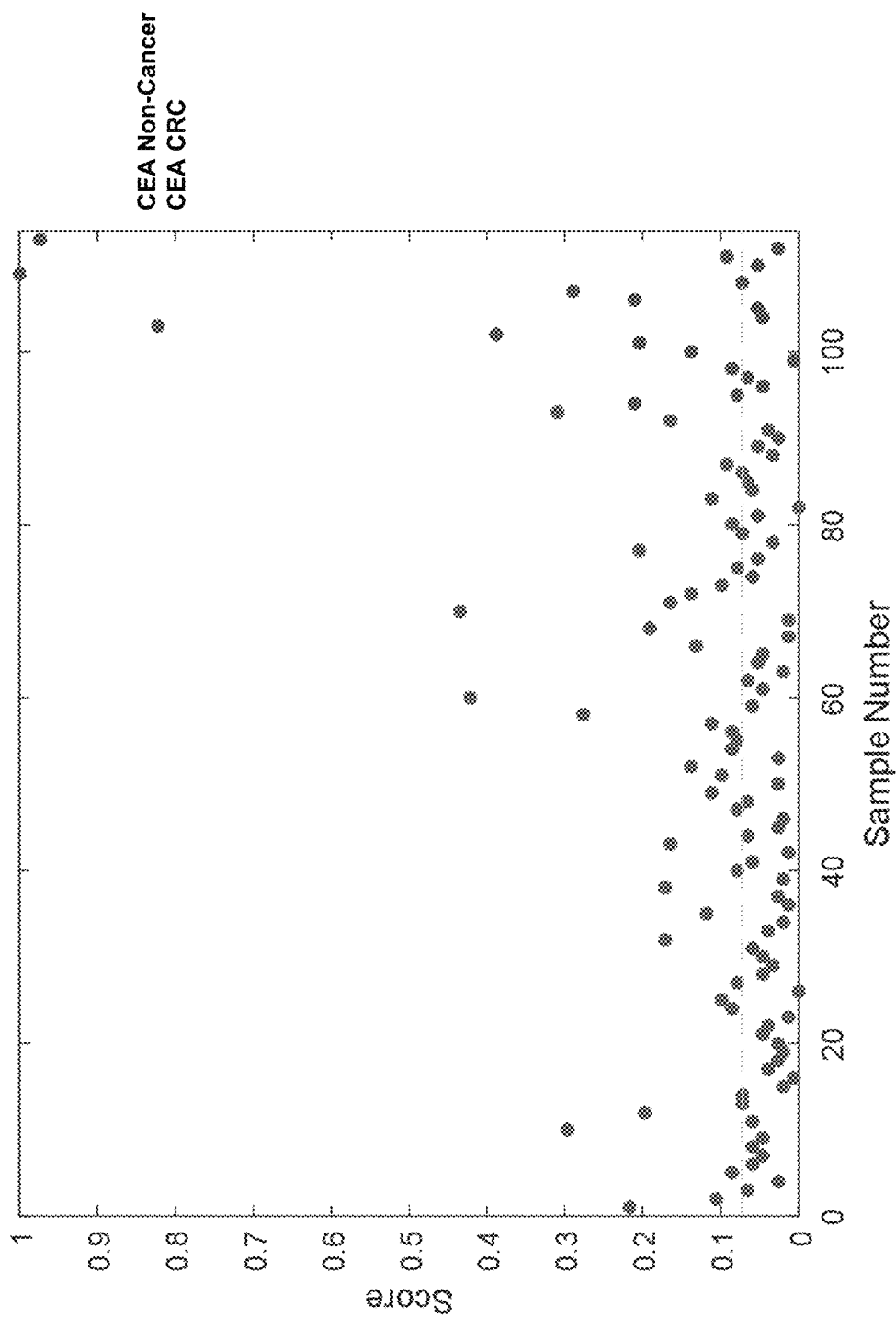
FIG. 6 illustrates a discrimination plot generated from measurement of a CEA biomarker alone in accordance with the instant disclosure.
Figure 7:
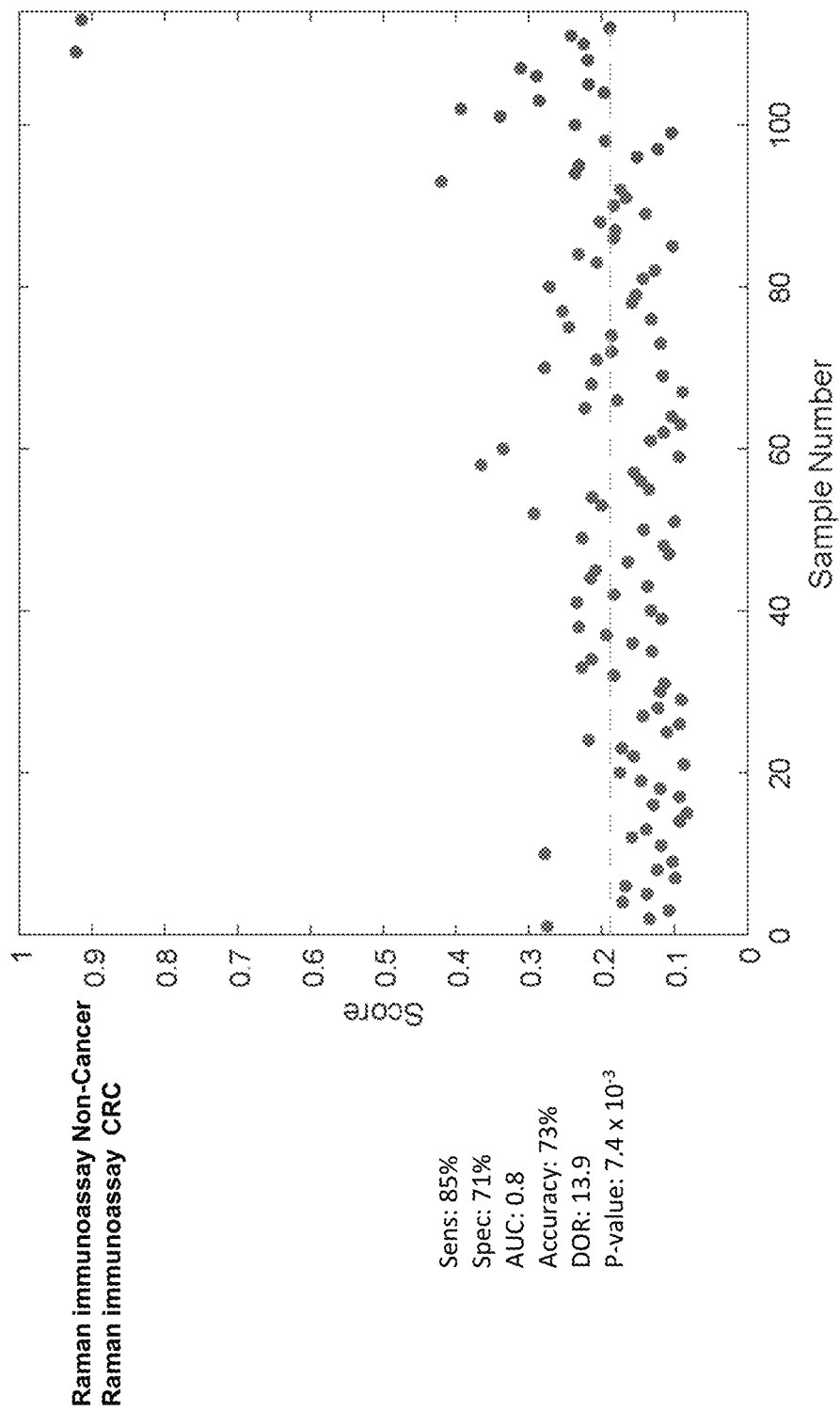
FIG. 7 illustrates a discrimination plot of a fused Raman and CEA biomarker data set in accordance with the instant disclosure.
Figure 8:
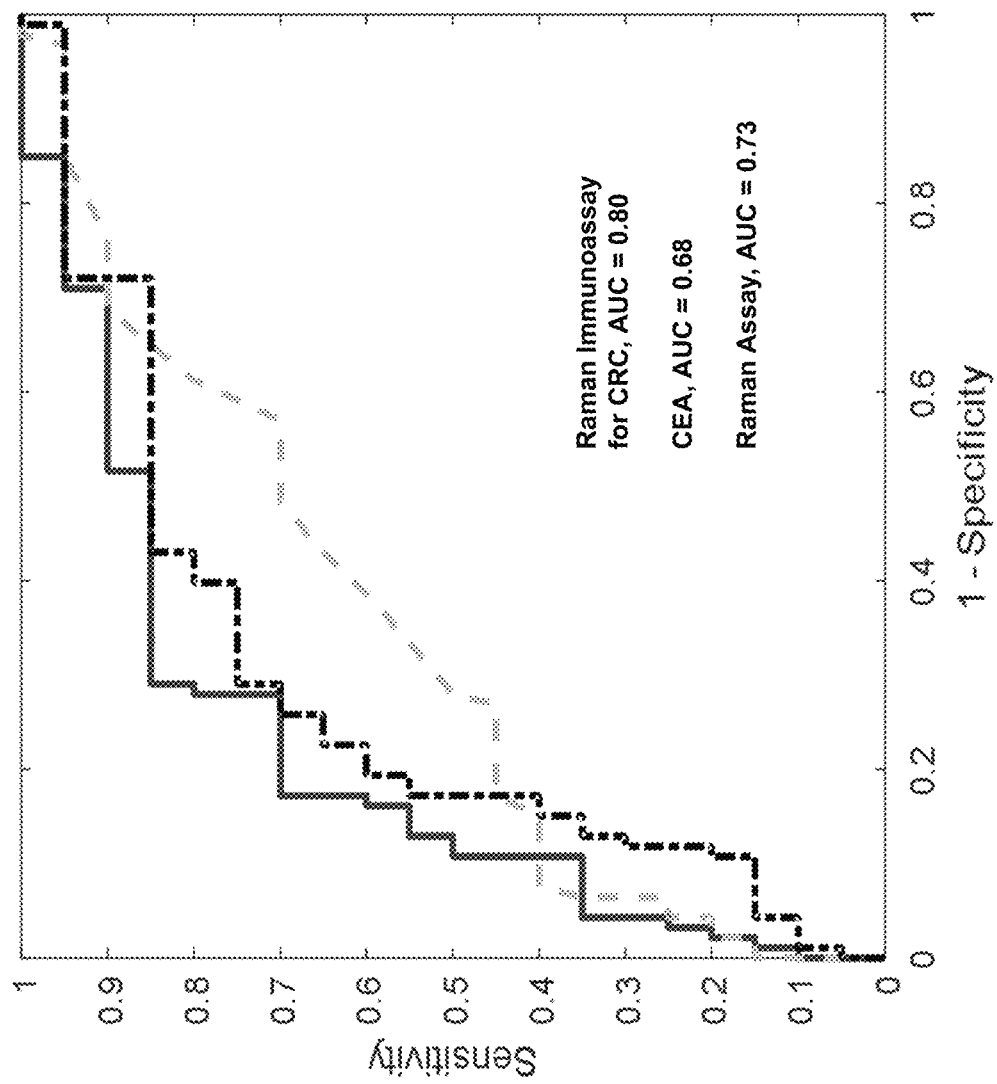
FIG. 8 illustrates the receiver operating characteristic (ROC) curves for the methodologies of FIGS. 5-7 in accordance with the instant disclosure.

FIGS. 5-8 show a comparison of a Raman data set alone ("Raman"), CEA biomarker data alone ("CEA"), and a Raman data set fused with CEA ("Fused") for detection of colorectal cancer ("CRC") versus non-cancer in patients. Non-cancer patients included those confirmed by colonoscopy to have negative findings, both with and without comorbidities. In FIG. 5, a discrimination plot representing Raman as a standalone methodology shows Raman indices for CRC and non-cancer blood samples. FIG. 6 shows the discrimination plot generated from measurement of CEA alone. The Fused protocol results in the discrimination plot shown in FIG. 7. ROC curves corresponding to the three methodologies are shown in FIG. 8. Of the three methods, measurement of CEA alone yields the lowest performance for detecting patients with CRC, with an AUC of 0.68. Raman, when used alone, performs better, with an AUC of 0.73. However, the overall performance of the Fused data showed a substantially increase, with a resulting AUC of 0.80—almost 10% higher than the AUC for Raman alone. Using the Fused data, sensitivity and specificity for the 113-patient study were 85% and 71%, respectively.

Similar results were observed when comparing Raman, CEA, and Fused data to the discrimination of CRC samples from clinical background samples (patients with colitis, benign gastrointestinal conditions, hyperplastic polyps, and colonoscopy-confirmed negative findings with and without comorbidities). Alone, Raman performance yields a ROC curve with an AUC of 0.72, and alone, CEA measurements result in a ROC curve with an AUC of 0.62. The Fused data yielded an increase in AUC of 8% to 0.78. The sensitivity and specificity for this 306-patient study for the Fused data was 75% and 71%, respectively.

Example 2

Table 1 and Table 2 show data related to the intra- and inter-assay variability of RMI. Intra-assay variability was established by producing an index value for five unique replicates of an individual sample that was confirmed CRC positive, the resulting variability was 0.05%. Inter-assay variability was established by producing an index value for one unique replicate from each of five samples confirmed CRC positive, the resulting variability was 0.21%. The low variability demonstrated suggests that RMI is a suitable method to be fused with IA.

TABLE 1

| Study ID | Index Value | % CV |
|---|---|---|
| S1_R1 | 0.9986 | |
| S1_R2 | 0.9996 | |
| S1_R3 | 0.9998 | |
| S1_R4 | 0.9997 | |
| S1_R5 | 0.9992 | |
| Mean | 0.9994 ± 0.0005 | 0.05% |

TABLE 2

| Study ID | Index Value | % CV |
|---|---|---|
| S1_R1 | 0.9951 | |
| S2_R1 | 0.9999 | |
| S3_R1 | 0.9996 | |
| S4_R1 | 0.9997 | |
| S5_R1 | 0.9999 | |
| Mean | 0.9989 ± 0.002 | 0.21% |

Example 3

Figure 9:
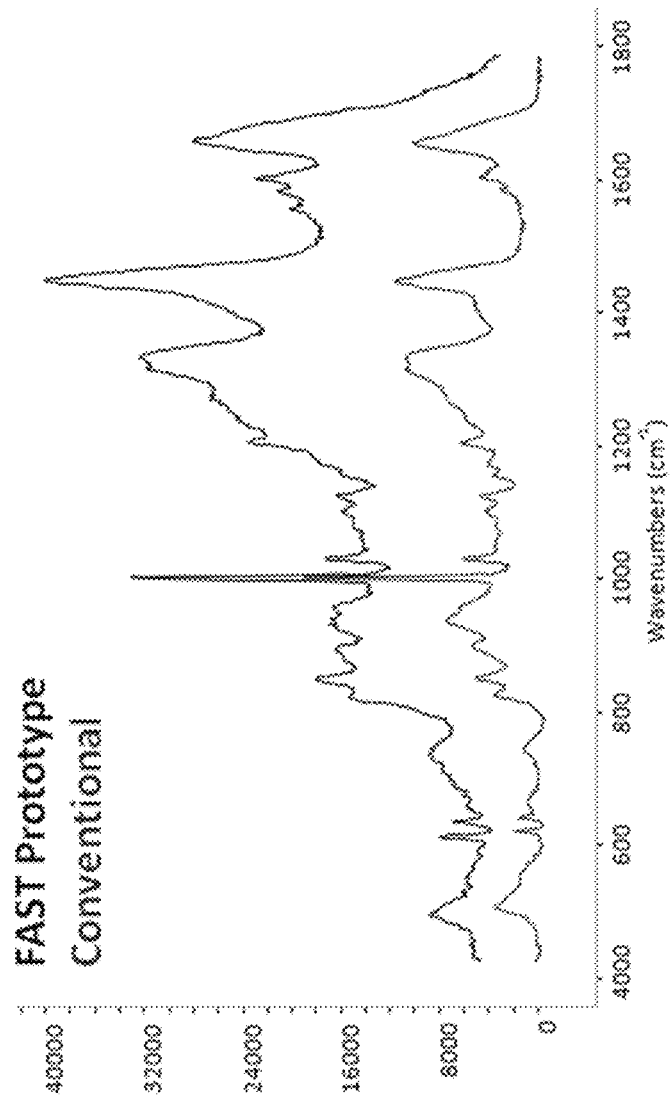
FIG. 9 illustrates a comparison of Raman spectra of human serum albumin (HSA) acquired using a FAST device versus a conventional confocal system in accordance with an embodiment.

FIG. 9 illustrates the advantages of FAST-based system compared to conventional confocal RMI data collection using an HSA sample. FIG. 9 shows the average spectrum from both methodologies. Table 3 shows a comparison of the salient features of each method. Importantly, a system including a FAST device reduces collection time from 22.5 min to 0.17 min with only a modest reduction in signal-to-noise ratio.

TABLE 3

| | FAST Prototype | Conventional |
|---|---|---|
| Laser Power (785 nm) | 500 mW | 100 mW |
| Photobleach Time | 0 secs | 30 secs |
| Acquisition Time | 10 secs | 60 secs |
| Max # Sampling Points | 96 | 1 |
| Sampling Area | 320X > G1.0 | $2.2 \times 10^{-7}$ cm$^2$ |
| HSA Amide I Signal | 22,276 counts | 10,155 counts |
| SNR | 87.3 | 101.0 |
| Throughput (Mins/Test) | 0.17 | 22.5 |

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

What is claimed is:

1. A system comprising:
   an illumination source configured to illuminate a biological sample and generate a plurality of interacted photons;
   a detector configured to detect the plurality of interacted photons and generate at least one Raman data set; and
   a processor configured to fuse the at least one Raman data set with at least one biomarker data set to identify one or more of a disease and a disease state.

2. The system of claim 1, further comprising:
   a fiber array spectral translator device configured to receive the plurality of interacted photons and generate an optical output, the fiber array spectral translator having a first end comprising a two-dimensional plurality of optical fibers and a second end comprising a one-dimensional stack of the plurality of optical fibers; and
   a spectrometer optically coupled to the one-dimensional stack and configured to filter the optical output into a plurality of wavelengths.

3. The system of claim 1, wherein the illumination source comprises a laser.

4. The system of claim 1, wherein the illumination source comprises a 785 nm laser.

5. The system of claim 1, further comprising a multiwall plate configured to hold a plurality of biological samples.

6. The system of claim 1, wherein the biological sample includes one or more of blood, serum, tissue, plasma, urine, semen, feces, and vaginal discharge.

7. The system of claim 1, wherein the biological sample includes dried blood.

8. The system of claim 1, wherein the at least one biomarker data set includes one or more of an inflammatory response and an immune response.

9. The system of claim 1, wherein the at least one biomarker data set includes a measure of a protein.

10. The system of claim 1, wherein the at least one biomarker data set includes a measure of one or more of a prostate-specific antigen and a carcinoembryonic antigen.

11. The system of claim 1, wherein the detector comprises one or more of a CCD detector, an ICCD detector, a CMOS detector, a PMT, a Si-avalanche photodiode, an InGaAs detector, an InSb detector, and an MCT detector.

12. The system of claim 1, wherein the Raman data set comprises one or more of a Raman spectrum and a Raman molecular image.

13. The system of claim 1, wherein the processor is configured to fuse the at least one Raman data set with the at least one biomarker data set by applying an algorithmic technique including one or more of a logistic regression, a partial least squares discriminant analysis, and an image weighted Bayesian fusion algorithm.

14. The system of claim 1, wherein the disease includes one or more of a cancer, an autoimmune disorder, and a neurodegenerative disorder.

15. The system of claim 1, wherein the at least one biomarker data set includes a measure of a plurality of biomarkers.

16. A method comprising:
   illuminating a biological sample to generate a plurality of interacted photons;
   detecting the plurality of interacted photons to generate at least one Raman data set;
   obtaining at least one biomarker data set from the biological sample; and
   fusing the at least one Raman data set with the at least one biomarker data set to generate an index score.

17. The method of claim 16, wherein the index score defines one or more of a disease and a disease state.

18. The method of claim 17, wherein the disease is cancer.

19. The method of claim 16, further comprising passing the plurality of interacted photons through a fiber array spectral translator.

20. The method of claim 16, wherein illuminating the biological sample includes illuminating with a laser.

21. The method of claim 20, wherein the laser has a wavelength of about 785 nm.

22. The method of claim 16, wherein detecting the plurality of interacted photons comprises detecting with one or more of a CCD detector, an ICCD detector, a CMOS detector, a PMT, a Si-avalanche photodiode, an InGaAs detector, an InSb detector, and an MCT detector.

23. The method of claim 16, wherein the at least one Raman data set comprises one or more of a Raman spectrum and a Raman image.

24. The method of claim 16, wherein the at least one biomarker data set comprises a measure of a cancer biomarker.

25. The method of claim 24, wherein the cancer biomarker includes one or more of a prostate specific antigen and a carcinoembryonic antigen.

26. The method of claim 16, wherein fusing the at least one Raman data set with the at least one biomarker data set includes applying an algorithmic technique including one or more of a logistic regression, a partial least squares discriminant analysis, and an image weighted Bayesian fusion algorithm.

27. The method of claim 16, wherein obtaining at least one biomarker data set comprises obtaining a measure of biomarker data from a plurality of biomarkers.

28. A system comprising:
an illumination source configured to illuminate a biological sample and generate a plurality of interacted photons;
a fiber array spectral translator device configured to receive the plurality of the interacted photons and generate an optical output, the fiber array spectral translator having a first end comprising a two-dimensional plurality of optical fibers and a second end comprising a one-dimensional stack of the plurality of optical fibers;
a spectrometer optically coupled to the one-dimensional stack and configured to filter the optical output into a plurality of wavelengths;
a detector configured to detect the optical output and generate at least one Raman data set; and
a processor configured to fuse the at least one Raman data set with at least one biomarker data set to identify one or more of a disease and a disease state.

29. The system of claim 28, further comprising a multi-wall plate configured to hold a plurality of biological samples.

30. The system of claim 28, wherein the biological sample includes dried blood.

31. The system of claim 28, wherein the at least one biomarker data set includes a measure of one or more of an inflammatory response and an immune response.

32. The system of claim 28, wherein the at least one biomarker data set includes a measure of a protein.

33. The system of claim 28, wherein the at least one biomarker data set includes a measure of one or more of a prostate-specific antigen and a carcinoembryonic antigen.

34. The system of claim 28, wherein the detector comprises one or more of a CCD detector, an ICCD detector, a CMOS detector, a PMT, a Si-avalanche photodiode, an InGaAs detector, an InSb detector, and an MCT detector.

35. The system of claim 28, wherein the Raman data set comprises one or more of a Raman spectrum and a Raman image.

36. The system of claim 28, wherein the processor is configured to fuse the at least one Raman data set with the at least one biomarker data set by applying an algorithmic technique including one or more of a logistic regression, a partial least squares discriminant analysis, and an image weighted Bayesian fusion algorithm.

37. The system of claim 28, wherein the disease includes cancer.

38. The system of claim 28, wherein the disease is selected from the group consisting of prostate cancer and colorectal cancer.

39. A method comprising:
illuminating a biological sample to generate a plurality of interacted photons;
passing the plurality of interacted photons through a fiber array spectral translator to generate an optical output;
detecting the optical output to generate at least one Raman data set;
obtaining at least one biomarker data set from the biological sample;
fusing the at least one Raman data set with the at least one biomarker data set to generate an index score.

40. The method of claim 39, wherein the index score defines one or more of a disease, a disorder, a disease progression, and a disorder progression.

41. The method of claim 40, wherein the disease is cancer.

42. The method of claim 39, wherein illuminating a biological sample includes illuminating with a laser.

43. The method of claim 42, wherein the laser has a wavelength of about 785 nm.

44. The method of claim 39, wherein detecting the optical output comprises detecting with one or more of a CCD detector, an ICCD detector, a CMOS detector, a PMT, a Si-avalanche photodiode, an InGaAs detector, an InSb detector, and an MCT detector.

45. The method of claim 39, wherein the at least one Raman data set comprises one or more of a Raman spectrum and a Raman molecular image.

46. The method of claim 39, wherein the at least one biomarker data set comprises a measure of a cancer biomarker.

47. The method of claim 46, wherein the cancer biomarker includes one or more of a prostate specific antigen and a carcinoembryonic antigen.

48. The method of claim 39, wherein fusing the at least one Raman data set with the at least one biomarker data set includes applying an algorithmic technique including one or more of a logistic regression, a partial least squares discriminant analysis, and an image weighted Bayesian fusion algorithm.

49. The method of claim 39, wherein obtaining at least one biomarker data set comprises obtaining a measure of biomarker data from a plurality of biomarkers.

50. A non-transitory storage medium containing machine readable program code, which when executed by a processor causes the processor to perform the following:
cause an illumination source to illuminate a biological sample to produce a plurality of interacted photons;
cause a fiber array spectral translator to collect the plurality of interacted photons and generate an optical output;
cause a detector to detect the optical output and generate at least one Raman data set; and
fuse the at least one Raman data set with at least one biomarker data set and generate an index score, wherein the index score indicates one or more of a disease, a disorder, a disease progression, and a disorder progression.

51. A system comprising:

a Raman imaging subsystem including:

an illumination source configured to illuminate a biological sample and generate a plurality of interacted photons; and a detector configured to detect the plurality of interacted photons and generate at least one Raman data set;

an immunoassay subsystem including:

at least one antibody pair corresponding to a biomarker of interest; and a secondary antibody including a color-based reporter component configured to generate a color having an intensity; and a processor configured to convert the color intensity to a biomarker index value and fuse the at least one Raman data set with the biomarker data index value to generate a Raman immunoassay index value.

\* \* \* \* \*